United States Patent
Takahashi et al.

(10) Patent No.: US 11,653,888 B2
(45) Date of Patent: May 23, 2023

(54) RADIOGRAPHIC IMAGING APPARATUS

(71) Applicant: Shimadzu Corporation, Kyoto (JP)

(72) Inventors: Wataru Takahashi, Kyoto (JP);
Hidetaka Takezawa, Kyoto (JP);
Michel Dargis, Laval (CA)

(73) Assignee: Shimadzu Corporation, Kyoto (JP)

( * ) Notice: Subject to any disclaimer, the term of this patent is extended or adjusted under 35 U.S.C. 154(b) by 141 days.

(21) Appl. No.: 16/652,888

(22) PCT Filed: Oct. 3, 2017

(86) PCT No.: PCT/JP2017/035936
§ 371 (c)(1),
(2) Date: Apr. 1, 2020

(87) PCT Pub. No.: WO2019/069360
PCT Pub. Date: Apr. 11, 2019

(65) Prior Publication Data
US 2020/0245964 A1    Aug. 6, 2020

(51) Int. Cl.
*A61B 6/00*    (2006.01)
*A61B 6/03*    (2006.01)
*G16H 30/40*    (2018.01)
*A61B 6/02*    (2006.01)

(52) U.S. Cl.
CPC .......... *A61B 6/5235* (2013.01); *A61B 6/022* (2013.01); *A61B 6/032* (2013.01); *A61B 6/463* (2013.01); *A61B 6/469* (2013.01); *A61B 6/481* (2013.01); *A61B 6/487* (2013.01); *A61B 6/5205* (2013.01); *A61B 6/54* (2013.01); *G16H 30/40* (2018.01)

(58) Field of Classification Search
None
See application file for complete search history.

(56) References Cited

U.S. PATENT DOCUMENTS

| | | | | |
|---|---|---|---|---|
| 2010/0061611 A1* | 3/2010 | Xu | ............. | G06T 7/136 382/131 |
| 2010/0266220 A1* | 10/2010 | Zagorchev | ............. | A61B 6/487 382/285 |
| 2010/0310140 A1* | 12/2010 | Schneider | ............. | G06T 7/35 382/130 |
| 2014/0003688 A1* | 1/2014 | Hansis | ............. | A61B 6/032 382/130 |
| 2015/0087972 A1* | 3/2015 | Dumont | ............. | A61B 5/318 600/431 |
| 2017/0124708 A1* | 5/2017 | Baumgart | ............. | A61B 6/487 |

FOREIGN PATENT DOCUMENTS

JP    2014-171790 A    9/2014

OTHER PUBLICATIONS

Written Opinion by the International Search Authority for PCT application PCT/JP2017/035936 dated Dec. 26, 2017, submitted with a machine translation.
Office Action, dated Feb. 15, 2023, issued in relation to corresponding Chinese Patent Application No. 201780094553.X together with an machine English translation thereof.

* cited by examiner

Primary Examiner — Angela M Hoffa
Assistant Examiner — Younhee Choi
(74) Attorney, Agent, or Firm — Muir Patent Law, PLLC

(57) ABSTRACT

This radiographic imaging apparatus (100) is provided with a control unit (5) configured to associate a projection image (70) in which at least a part of a post-removal projection image (70a) in which a contrast agent image (Ba) has been removed and at least a part of a fluoroscopic image (20) are most similar.

15 Claims, 11 Drawing Sheets

RADIOGRAPHIC IMAGING APPARATUS

TECHNICAL FIELD

The present invention relates to a radiographic imaging apparatus.

BACKGROUND ART

Conventionally, there is known a radiographic imaging apparatus capable of generating a radiation image by detecting radiation that has transmitted through a subject. Such a radiographic imaging apparatus is disclosed in, for example, Japanese Unexamined Patent Application Publication No. 2014-171790.

In Japanese Unexamined Patent Application Publication No. 2014-171790, a radiographic imaging apparatus provided with an imaging unit having a radiation source and a detection means, an arm supporting the imaging unit, a moving image generation means, and a three-dimensional image acquisition means is disclosed. The moving image generation means generates a two-dimensional moving image by connecting a series of two-dimensional radiation images obtained by sequentially imaging a subject with the imaging unit in the order of imaging. The three-dimensional image acquisition means acquires a three-dimensional image of the subject based on a series of radiation images acquired by imaging while rotating the imaging unit with the arm.

The radiographic imaging apparatus disclosed in Japanese Unexamined Patent Application Publication No. 2014-171790 is configured such that a stereoscopic image of a subject is preliminary captured at an arbitrary point of time by an external CT imaging apparatus before capturing a two-dimensional moving image and then the positional displacement between the stereoscopic image and the three-dimensional image acquired by the imaging unit is obtained. The radiographic imaging apparatus disclosed in Japanese Unexamined Patent Application Publication No. 2014-171790 is configured to generate a projection image obtained by projecting a stereoscopic image in which the positional displacement has been corrected on a two-dimensional plane when capturing a two-dimensional moving image, superimpose the projection image on the moving image, and display the superimposed image. Here, the stereoscopic image of the subject acquired in advance prior to the capturing of the moving image includes an image of a contrast agent administered to the subject when capturing the image.

PRIOR ART

Patent Document

Patent Document 1: Japanese Unexamined Patent Application Publication No. 2014-171790

SUMMARY OF THE INVENTION

Problems to be Solved by the Invention

However, in a radiographic imaging apparatus disclosed by, e.g., Japanese Unexamined Patent Application Publication No. 2014-171790, the projection image generated from a stereoscopic image of a subject acquired in advance is only a still image captured at an arbitrary point of time. For this reason, when the radiographic imaging apparatus disclosed in, e.g., Japanese Unexamined Patent Application Publication No. 2014-171790 is used for imaging in the case of, e.g., a percutaneous coronary intervention (PCI) in which blood vessels are periodically moved due to a heartbeat of a patient while performing X-ray fluoroscopic imaging of the patient, there is a problem that the image of the contrast agent in the projection image to be superimposed may displaced from the actual blood vessel position.

The present invention has been made to solve the aforementioned problems, and one object of the present invention is to provide a radiographic imaging apparatus capable of suppressing a displacement between an actual position of an blood vessel and a position of an image of a contrast agent to be superimposed even in the case of imaging a periodically moving blood vessel.

Means for Solving the Problems

In order to attain the aforementioned object, a radiographic imaging apparatus according to one aspect of the present invention comprises:

an irradiation unit configured to irradiate a subject with radiation so that a region-of-interest in the subject is included therein;

a detection unit configured to detect the radiation which has transmitted through the subject;

an image generation unit configured to generate a fluoroscopic image including the region-of-interest based on an output of the detection unit;

a display unit configured to display the fluoroscopic image;

a projection image generation unit configured to generate a two-dimensional projection images, the projection images each derived from three dimensional images collected at multiple points of time with a contrast agent being administered to at least a part of the region-of-interest;

a control unit configured to associate one of the generated projection images with the fluoroscopic image;

a superimposed image generation unit configured to generate a superimposed image by superimposing the fluoroscopic image and the projection image associated with the fluoroscopic image; and a display unit configured to display the superimposed image, wherein the control unit is operable to associate one of the projection images with the fluoroscopic image, the one projection image having the highest degree of similarities between at least a part of a post-removal projection image in which an image of the contrast agent is removed and at least a part of the fluoroscopic image.

In the X-ray imaging apparatus according to one aspect of the present invention, as described above, the control unit associates the projection image in which at least a part of a post-removal projection image in which an image of the contrast agent has been removed and at least a part of the fluoroscopic image are most similar. With this, it is possible to superimpose the projection image in which at least a part of the generated projection image is most similar to at least a part of the fluoroscopic image on the fluoroscopic image and display the superimposed image. As a result, for example, even in cases where a periodically moving blood vessel is included in the region-of-interest, the positional displacement between the actual blood vessel and the image of the contrast agent to be superimposed can be suppressed. Accordingly, even in a moving image generated by connecting fluoroscopic images, it is possible to display the image of the contrast agent in a superimposed manner with the displacement from the position of the actual blood sell suppressed. In addition, when associating a fluoroscopic image with a projection image, since the post-removal projection image in which the image of the contrast agent has been removed is used, it is possible to exclude the image of the contrast agent that is not used to associate the fluoroscopic image with the projection image. This makes it easier to identify the feature points used for the above association other than the image of the contrast agent reflected in the projection image. As a result, it is possible to easily associate the fluoroscopic image with the projection image.

In the radiographic imaging apparatus according to one aspect described above, preferably, the projection image generation unit generates the two-dimensional projection image from each of the stereoscopic images of the subject collected from the outside at the multiple points of time. By configuring as described above, the stereoscopic image of the subject can be collected using a device which is different from the radiographic imagining apparatus and suitable for acquiring the stereoscopic images of the subject by sequentially acquiring the stereoscopic images of the subject at multiple points of time. As a result, there is no need to provide a configuration for sequentially capturing stereoscopic images of the subject different from the configuration for performing X-ray fluoroscopic imaging in the radiographic imaging apparatus.

In the radiographic imaging apparatus according to one aspect of the present invention, preferably, the projection image generation unit generates the two-dimensional projection image from the stereoscopic image so that at least an orientation of the subject in the stereoscopic image substantially matches an orientation of the subject whose fluoroscopic image is to be generated. By configuring as described above, even in cases where the orientation of the subject in the collected stereoscopic image does not match the current orientation of the subject for generating the fluoroscopic image, it is possible to associate the projection image projected from the stereoscopic image adjusted so that the orientation of the subject in the collected stereoscopic image matches the current orientation of the subject with the fluoroscopic image. As a result, it is possible to more accurately associate the fluoroscopic image with the projection image.

In the radiographic imaging apparatuses according to one aspect of the present invention described above, preferably, the region-of-interest includes a region that periodically moves due to a heartbeat or a respiratory beat. Note that a heartbeat or a respiratory beat causes a periodic movement of a blood vessel. For this reason, in cases where a region that moves periodically due to a heartbeat or a respiratory beat is included in the region-of-interest, it is likely to cause a positional displacement between the actual blood vessel and the image of the contrast agent to be superimposed. Accordingly, it is particularly effective to apply the present invention in which a fluoroscopic image containing a region-of-interest is generated and a projection image in which at least a part of the projection image is most similar to at least a part of the fluoroscopic image is superimposed on the fluoroscopic image to a radiographic imaging apparatus configured to image the subject so that a periodically moving region due to a heartbeat or a respiratory beat is included.

Preferably, in the configuration in which the region-of-interest includes a periodically moving region, preferably, the stereoscopic image is collected so that at least one cycle of a periodic motion of the periodically moving region is included. By configuring as described above, it is possible to suppress the case in which there exists no projection image similar to the fluoroscopic image with respect to a periodically moving region in the region-of-interest. As a result, it is possible to assuredly superimpose a projection image whose periodically moving region is most similar to a fluoroscopic image among generated projection images on the fluoroscopic image and display the superimposed image.

In the radiographic imaging apparatuses according to one aspect of the present invention described above, preferably, the stereoscopic image is acquired by CT imaging. By configuring as described above, stereoscopic images of the subject at multiple points of time can be easily obtained by CT imaging suitable for sequential capturing the stereoscopic image of the subject.

Effects of Invention

According to the present invention, even in the case of imaging a periodically moving blood vessel as described above, it is possible to provide a radiographic imaging apparatus capable of suppressing the positional displacement between the actual blood vessel and the image of the contrast agent to be superimposed.

EMBODIMENTS FOR CARRYING OUT THE INVENTION

Hereinafter, embodiments of the present invention will be described with reference to the drawings.
(Configuration of X-Ray Fluoroscopic Imaging Apparatus)

With reference to FIG. 1 to FIG. 10, the configuration of an X-ray fluoroscopic imaging apparatus 100 according to an embodiment of the present invention will be described. The X-ray fluoroscopic imaging apparatus 100 is an apparatus for performing a percutaneous coronary intervention while performing X-ray fluoroscopic imaging of a patient. The X-ray fluoroscopic imaging apparatus 100 is an apparatus capable of superimposing an image acquired in advance by a CT imaging apparatus (not shown) on an X-ray fluoroscopic image and displaying the superimposed image. Note that the X-ray fluoroscopic imaging apparatus 100 is an example of the "radiographic imaging apparatus" recited in claims.

Figure 1:
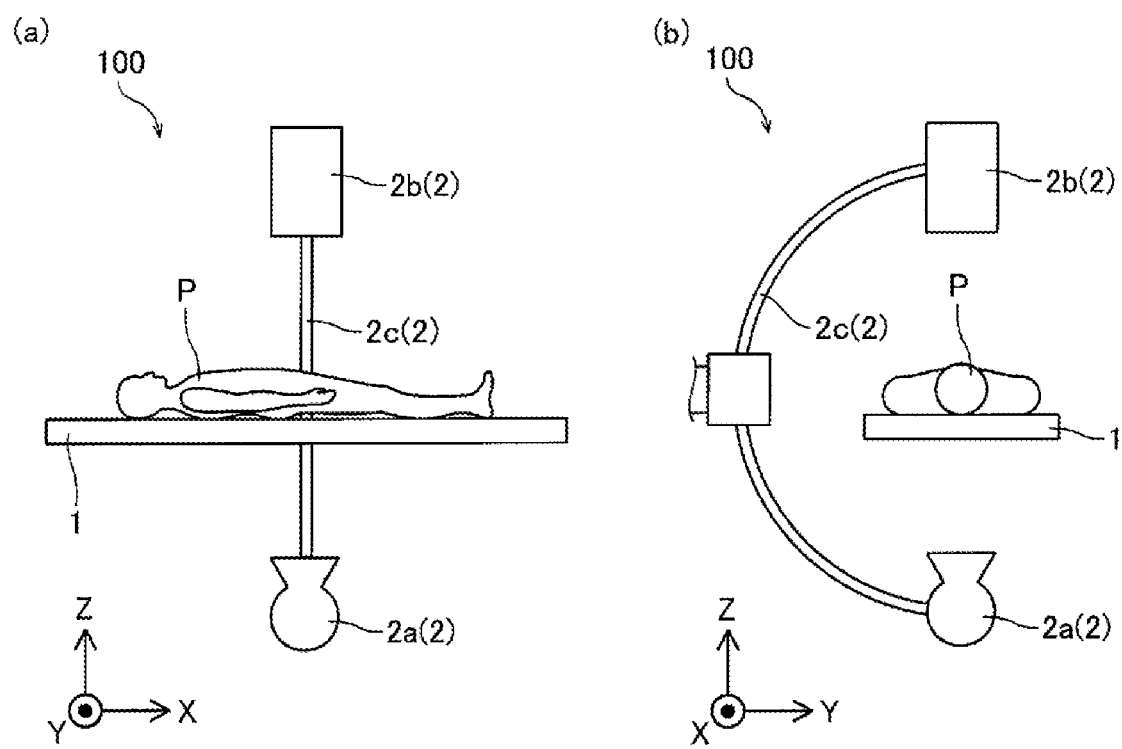
FIG. 1 shows an overview of an X-ray fluoroscopic imaging apparatus according to an embodiment of the present invention.

As shown in FIG. 1, the X-ray fluoroscopic imaging apparatus 100 according to this embodiment is provided with a top board 1 for placing a subject P thereon and an imaging unit 2 for performing fluoroscopic imaging or X-ray imaging of the subject P.

The top board 1 is formed in a rectangular flat plate shape in a plan view. A subject P is placed on the top board 1 so that the head-to-foot orientation of the subject P matches the orientation along which the long side of the rectangle extends (the longitudinal direction of the top board 1) and that the left-right orientation of the subject P matches the direction along which the short side of the rectangle extends (the short direction of the top board 1). Note that in this specification, the longitudinal direction of the top board 1 is defined as an X-axis direction, the short direction of the top board 1 is defined as a Y-axis direction, and the direction orthogonal to the X-axis direction and the Y-axis direction is defined as a Z-axis direction.

The imaging unit 2 is provided with an X-ray source, an X-ray tube device 2a disposed on one side of the top board 1, an X-ray receiver 2b disposed on the other side of the top board 1, and a C-shaped arm portion 2c supporting the X-ray tube device 2a and the X-ray receiver 2b. The X-ray tube device 2a and the X-ray receiver 2b are an example of the "irradiation unit" and an example of the "detection unit" recited in claims, respectively.

The X-ray tube device 2a is provided with an X-ray source and is configured to emit X-rays when a voltage is applied by an X-ray tube drive unit (not shown). The X-ray receiver 2b is provided with an FPD (flat panel detector), and is configured to detect X-rays. With this configuration, the X-ray fluoroscopic imaging apparatus 100 can perform X-ray fluoroscopic imaging or X-ray imaging by irradiating the subject P with X-rays by the X-ray tube device 2a so that the region-of-interest is included in a state in which the subject P is placed on the top board 1 and detecting the X-rays that have transmitted through the subject P. Note that the region-of-interest may include, for example, a region that periodically moves due to the heartbeat or the respiratory beat of the subject P.

The arm portion 2c is configured to be rotatably driven in the Z-Y plane by an imaging unit drive mechanism (not shown) about a position near the top board 1 on which the subject P is placed as a rotation axis. With this, it is possible to perform X-ray fluoroscopic imaging or X-ray imaging of the subject P placed on the top board 1 in a state in which the X-ray tube device 2a and the X-ray receiver 2b are each arranged at an arbitrary position in the Y-Z plane.

Figure 2:
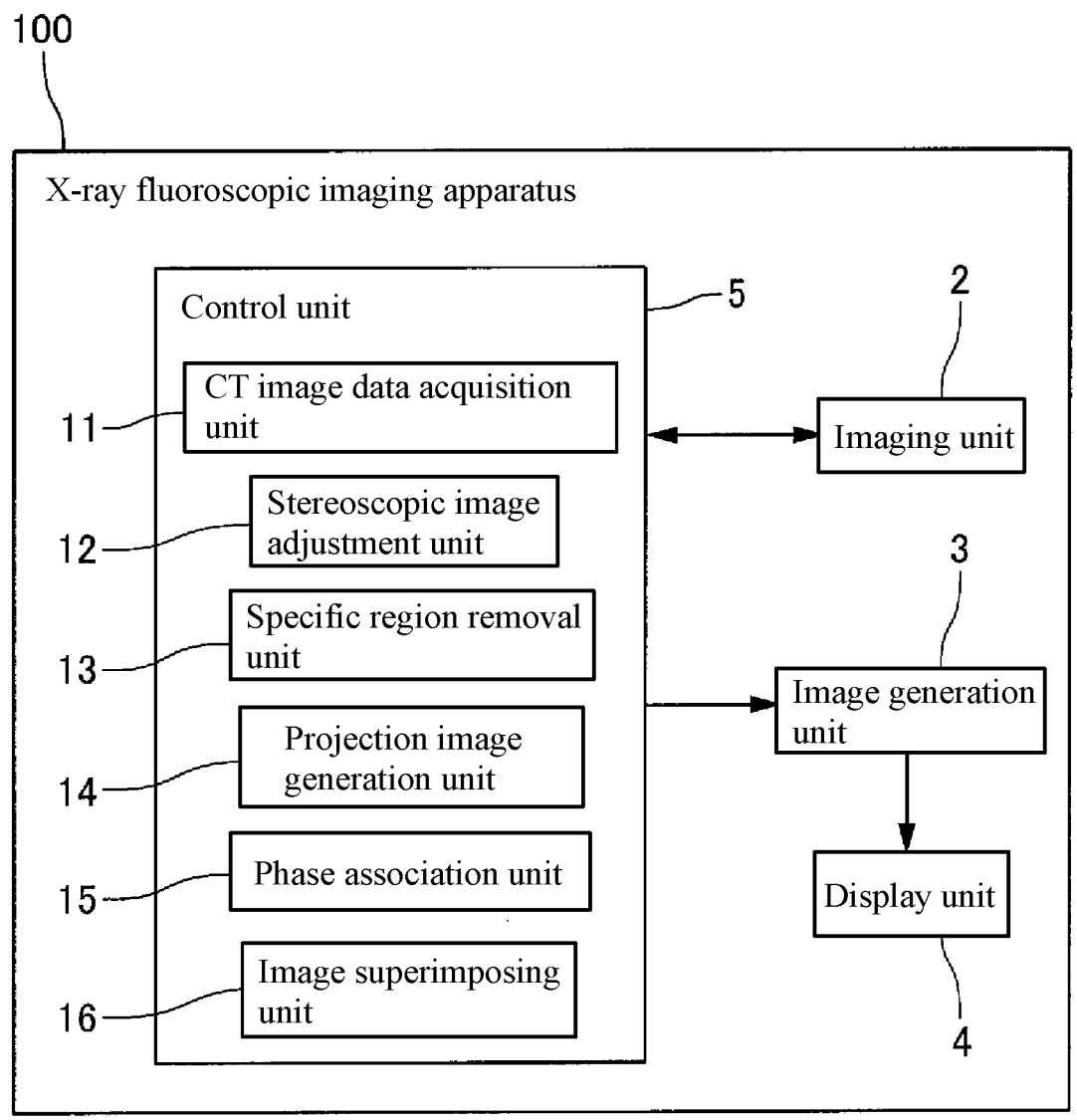
FIG. 2 is a block diagram showing the configuration of a control system of the X-ray fluoroscopic imaging apparatus according to an embodiment of the present invention.
Figure 3:
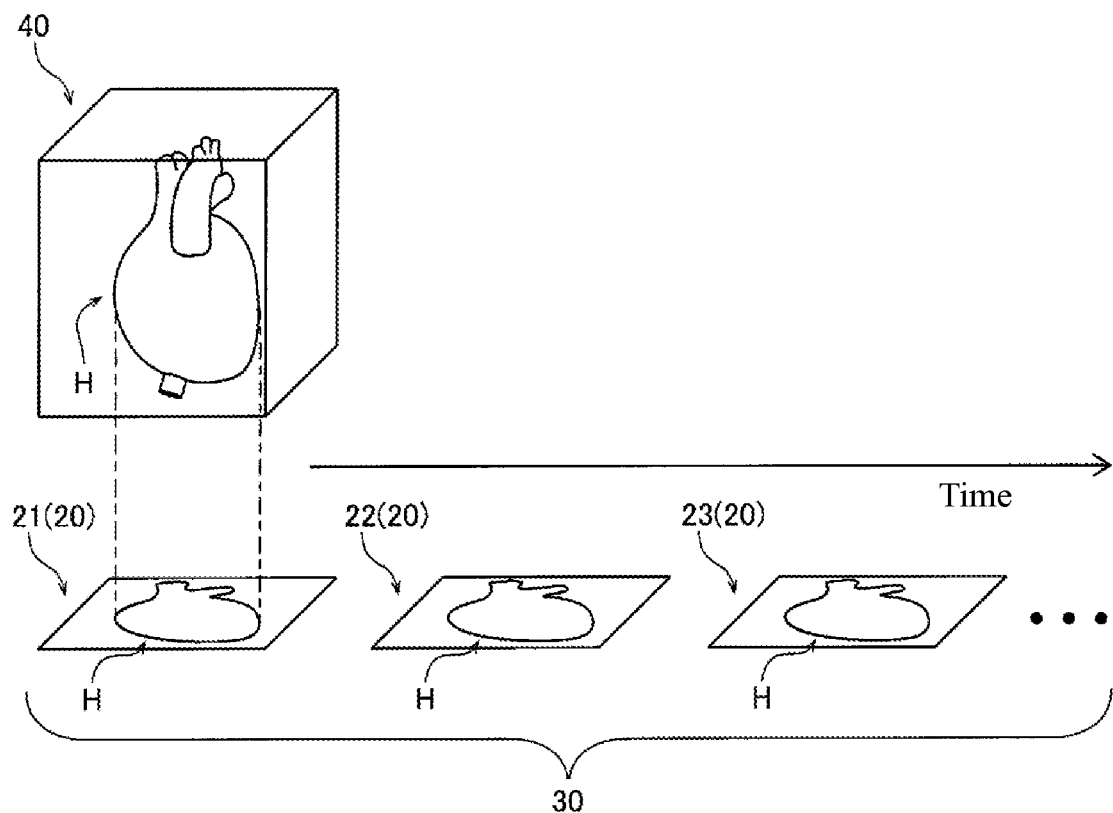
FIG. 3 is a diagram for explaining a fluoroscopic image, a moving image, and a three-dimensional image.

As shown in FIG. 2, the X-ray fluoroscopic imaging apparatus 100 is further provided with an image generation unit 3, a display unit 4, and a control unit 5. The image generation unit 3 is configured to generate an image based on X-rays (radiation) detected by the X-ray receiver 2b. The display unit 4 is configured to display an image generated in the image generation unit 3. The control unit 5 is configured to perform the control for superimposing an image acquired in advance by a CT imaging apparatus on the X-ray fluoroscopic image and displaying the superimposed image.

Based on the detection signal sent from the X-ray receiver 2b, the image generation unit 3 is configured to generate a two-dimensional fluoroscopic image 20 (see FIG. 3) obtained by performing X-ray fluoroscopic imaging of the internal structure of the subject P so that the region-of-interest is included. Further, the image generation unit 3 is configured such that a moving image 30 (see FIG. 3) can be generated by connecting a series of fluoroscopic images 20 (21, 22, 23, . . . ) generated by sequentially imaging the subject P in the imaging order. Further note that it is configured such that a three-dimensional image 40 (see FIG. 3) showing the internal structure of the subject P can be generated by performing X-ray fluoroscopic imaging of the subject P while rotating the imaging unit 2 in the Y-Z plane. In the fluoroscopic image 20 and the three-dimensional image 40, an example is shown in which X-ray fluoroscopic imaging is performed so that the heart H of the subject P is reflected.

The display unit 4 is configured by, for example, a liquid crystal display. The display unit 4 is configured to display the fluoroscopic image 20, the moving image 30, and the three-dimensional image 40 generated by the image generation unit 3.

The control unit 5 is a computer configured to include a CPU (Central Processing Unit), a ROM (Read Only Memory), a RAM (Random Access Memory), and the like.

The control unit 5 is provided with a CT image data acquisition unit 11, a stereoscopic image adjustment unit 12, a specific region removal unit 13, a projection image generation unit 14, a phase association unit 15, and an image superimposing unit 16. Note that the image superimposing unit 16 is an example of the "superimposed image generation unit" recited in claims.

Figure 4:
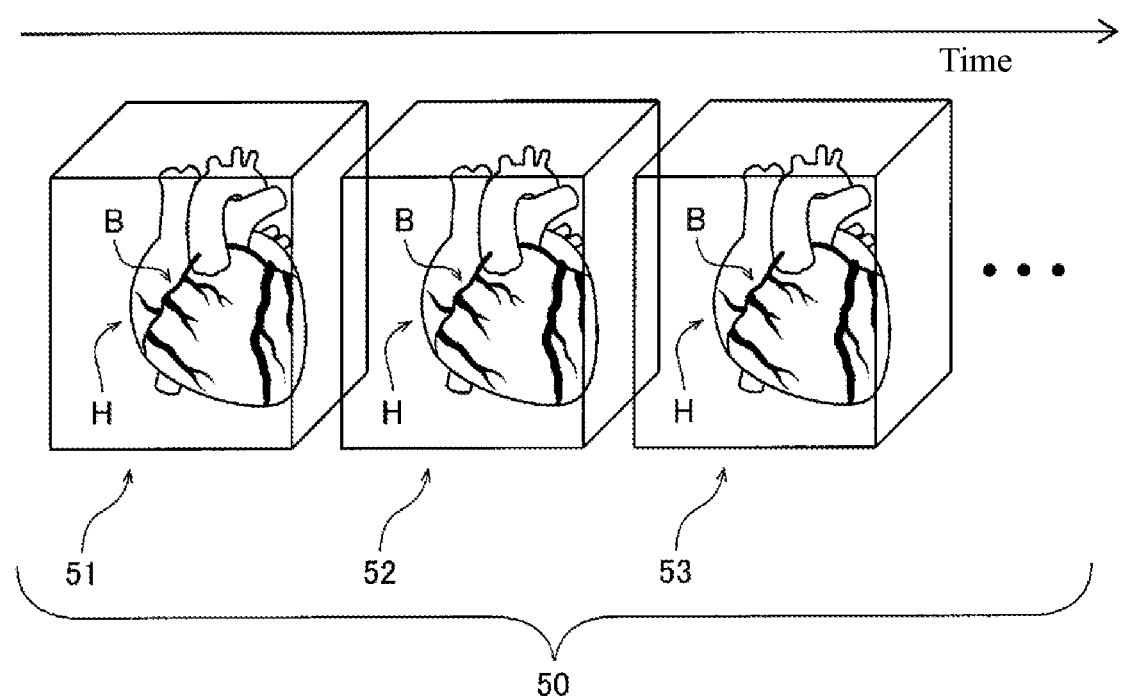
FIG. 4 is a diagram for explaining stereoscopic images at multiple points of time by CT imaging.

The CT image data acquisition unit 11 is configured to acquire the data of the stereoscopic image 50 (see FIG. 4) of the subject P from a CT imaging apparatus suitable for CT imaging and different from the X-ray fluoroscopic imaging apparatus 100 (for example, an external apparatus). Here, the CT imaging apparatus is an apparatus capable of sequentially performing tomographic imaging of the subject P. Accordingly, as shown in FIG. 4, the CT image data acquisition unit 11 can acquire (collect) stereoscopic images 50 (51, 52, 53, . . . ) sequentially captured at multiple points of time. Note that in the CT imaging apparatus, CT imaging may be performed in a state in which a contrast agent has been administered to the subject P. With this, the CT image data acquisition unit 11 can acquire (collect) a stereoscopic image 50 including a clear image B of the contrast agent as shown in FIG. 4. Here, the stereoscopic image 50 represents the internal structure of the subject P as three-dimensional voxel data.

The stereoscopic image adjustment unit 12 is configured such that the orientation and position of the stereoscopic image 50 of the subject P acquired by the CT image data acquisition unit 11 can be adjusted based on the three-dimensional image 40. The CT imaging apparatus is an apparatus different from the X-ray fluoroscopic imaging apparatus 100. Therefore, it is considered that the posture of the subject P imaged by the CT imaging apparatus and the posture of the subject P imaged by the X-ray fluoroscopic imaging apparatus 100 normally do not match with each other. For example, as shown in (a) of FIG. 5, the orientation and position of the heart H of the subject P in the stereoscopic image 50 and the orientation and position of the three-dimensional image 40 are different.

Figure 5:
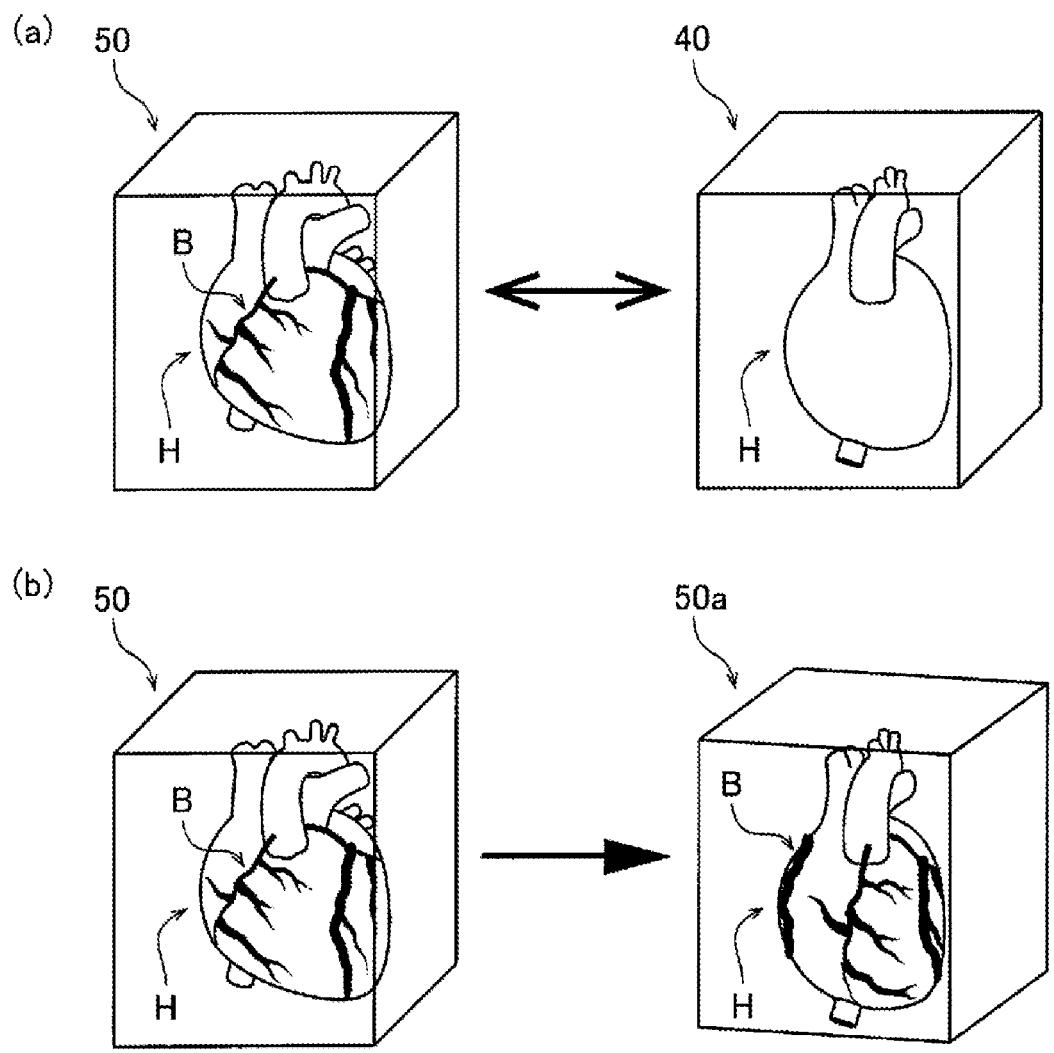
FIG. 5 is a diagram for explaining the adjustment of the position and orientation of a stereoscopic image based on a three-dimensional image.

Therefore, the stereoscopic image adjustment unit 12 is configured to generate an adjusted stereoscopic image 50a as shown in (b) of FIG. 5. The adjusted stereoscopic image 50a is obtained by adjusting the orientation and position of the subject P in the stereoscopic image 50 based on the three-dimensional image 40 on the basis of the region around the heart H with less periodic movements. For example, the stereoscopic image adjustment unit 12 calculates, based on a plurality of feature points in the ribs and spine around the heart H, an adjustment value for adjusting the orientation and position of the stereoscopic image 50 by rotating and/or translating the stereoscopic image 50 so that the orientation and position of the ribs and spine around the heart H of the subject P reflected in the stereoscopic image 50 match the orientation and position of the ribs and spine around the heart H of the subject P reflected in the three-dimensional image 40 based on the ribs and spine (not shown) around the heart H of the subject P reflected in the stereoscopic image 50. The stereoscopic image adjustment unit 12 generates a series of adjusted stereoscopic images 50a each obtained by adjusting the data of each of sequentially captured stereoscopic images 50 based on the calculated adjustment value as shown in (b) of FIG. 5.

Figure 6:
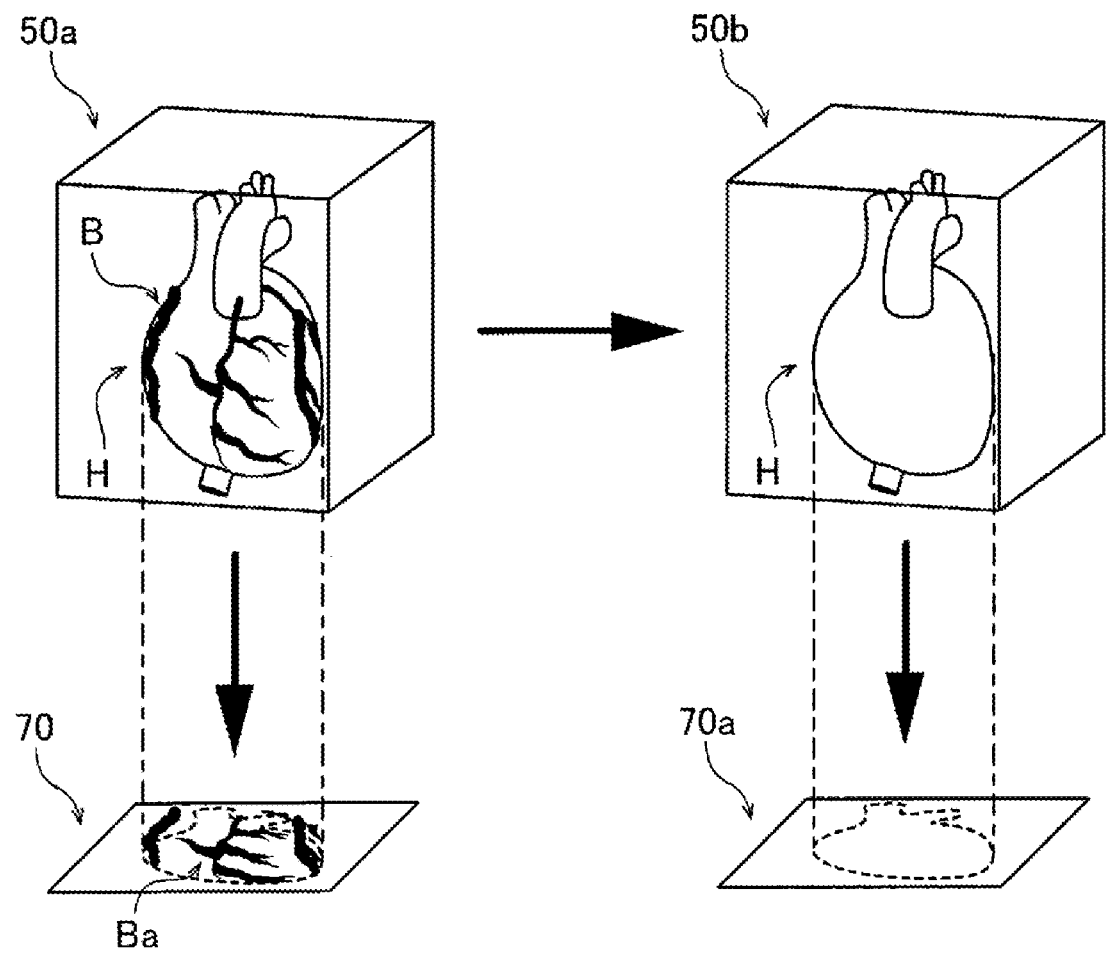
FIG. 6 is a diagram for explaining processing of removing an image of a contrast agent from a stereoscopic image and processing of generating a projection image obtained by two-dimensionally projecting the stereoscopic image.

The specific region removal unit 13 is configured to remove only the data of a particular voxel based on the CT value (the numerical value of the X-ray absorption coefficient) from the stereoscopic image 50 obtained from the CT imaging apparatus. With this, the specific region removal unit 13 can generate a series of post-removal stereoscopic images 50b in which the image B of the contrast agent has been removed from a series of adjusted stereoscopic images 50a based on the data of the stereoscopic image 50, as shown in FIG. 6.

The projection image generation unit 14 is configured to two-dimensionally project the stereoscopic image 50. That is, the projection image generation unit 14 can generate a two-dimensional projection image 70 from each of the stereoscopic images 50 collected at multiple points of time. Accordingly, the projection image generation unit 14 can generate a projection image 70 in which the image Ba of the contrast agent is reflected by two-dimensionally projecting the image B of the contrast agent, as shown in FIG. 6. Further, the projection image generation unit 14 can generate a series of post-removal projection images 70a in which no image B of the contrast agent is reflected from the post-removal stereoscopic image 50b. Note that the projection image 70 (post-removal image 70a) is a two-dimensional pixel data converted from the stereoscopic image 50 (post-removal stereoscopic image 50b), which represents the internal structure of the subject P as three-dimensional voxel data. Further note that in the projection image 70, the image B of the contrast agent, which had been three-dimensionally reflected in the stereoscopic image 50, is reflected as a two-dimensional image Ba of the contrast agent.

Figure 7:
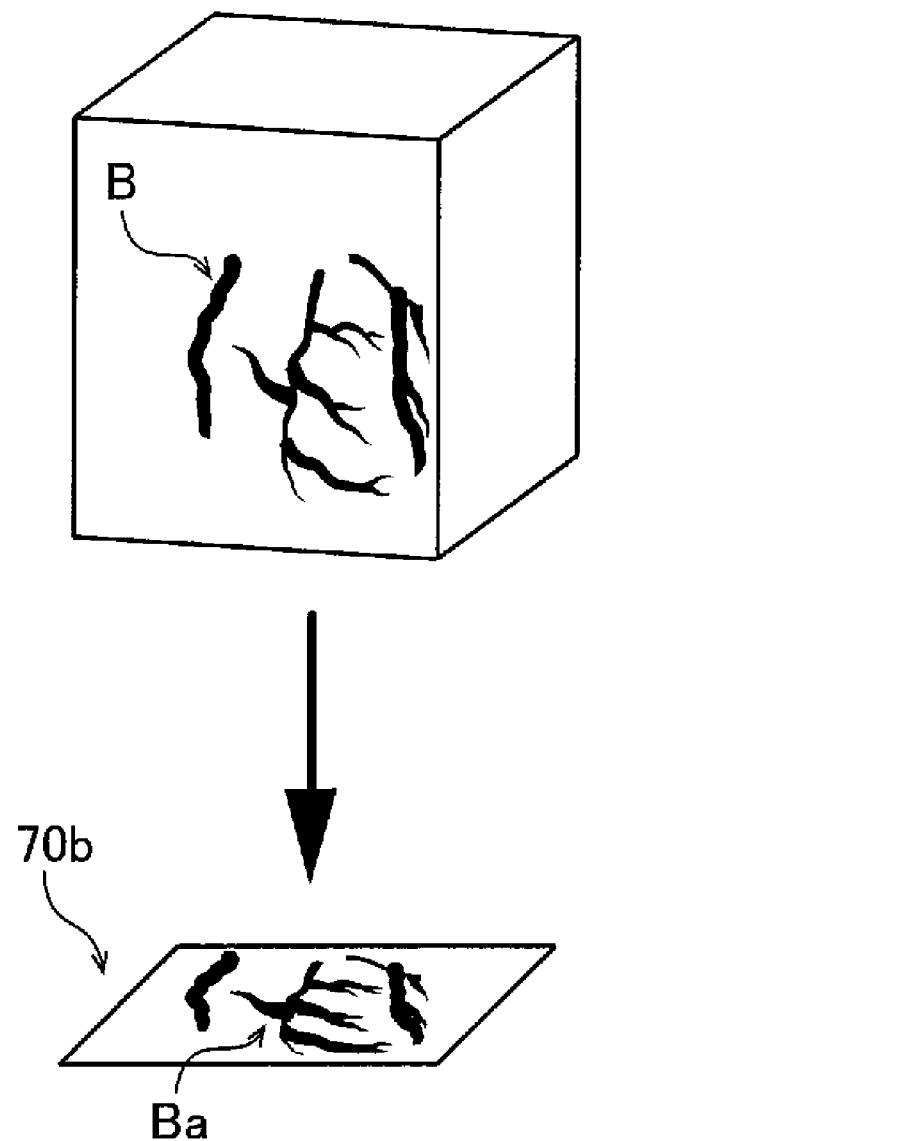
FIG. 7 is a diagram for explaining processing for generating a projection image obtained by two-dimensionally projecting the image of a contrast agent extracted from a stereoscopic image.

The projection image generation unit 14 can also generate a superimposing projection image 70b in which a portion other than the image Ba of the contrast agent has been removed by two-dimensionally projecting the image B of the contrast agent extracted from the adjusted stereoscopic image 50a, as shown in FIG. 7. Note that the superimposing projection image 70b is used to be superimposed on the fluoroscopic image 20. The projection image to be superimposed on the fluoroscopic image 20 may be either the projection image 70 or the superimposing projection image 70b, but the superimposing projection image 70b in which only the image Ba of the contrast agent is reflected is preferable than the projection image 70 in which portions other than the image Ba of the contrast agent are also reflected. Also note that it is enough that the projection image generation unit 14 generates only one of the projection image 70 and the superimposing projection image 70b to superimpose it on the fluoroscopic image 20.

Figure 8:
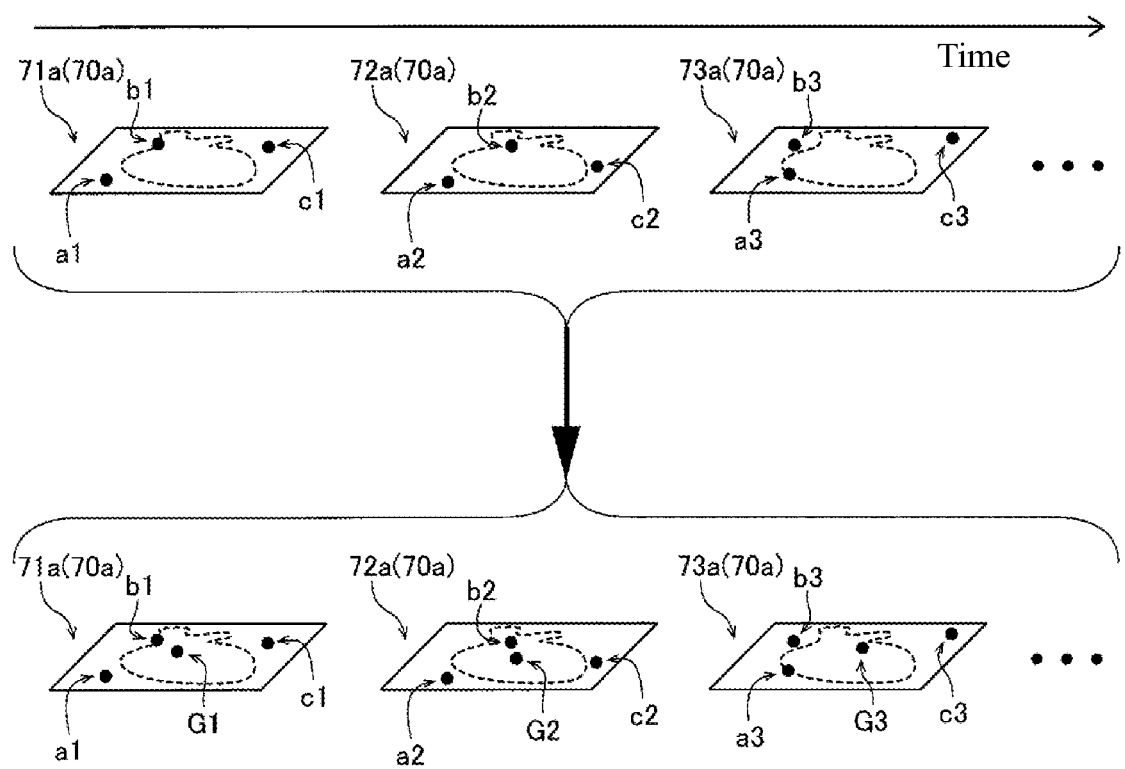
FIG. 8 is a diagram for explaining periodically moving regions in a projection image.
Figure 9:
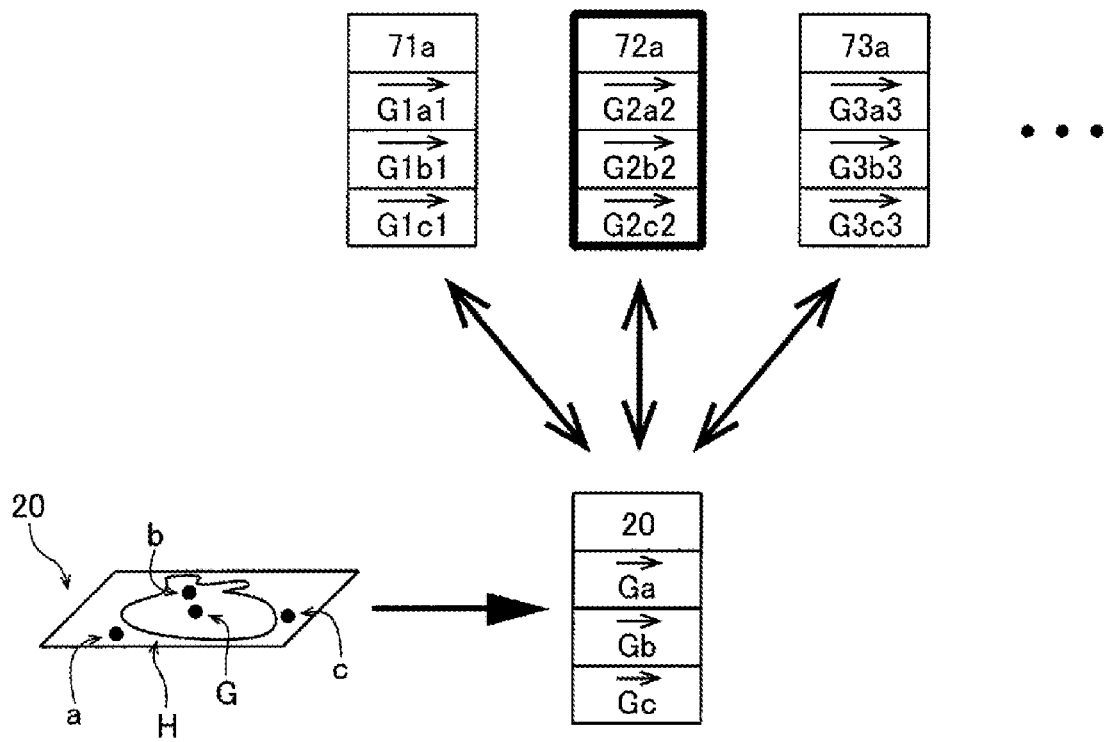
FIG. 9 is a diagram for explaining phase alignment between a fluoroscopic image and a stereoscopic image based on a periodically moving region.
Figure 10:
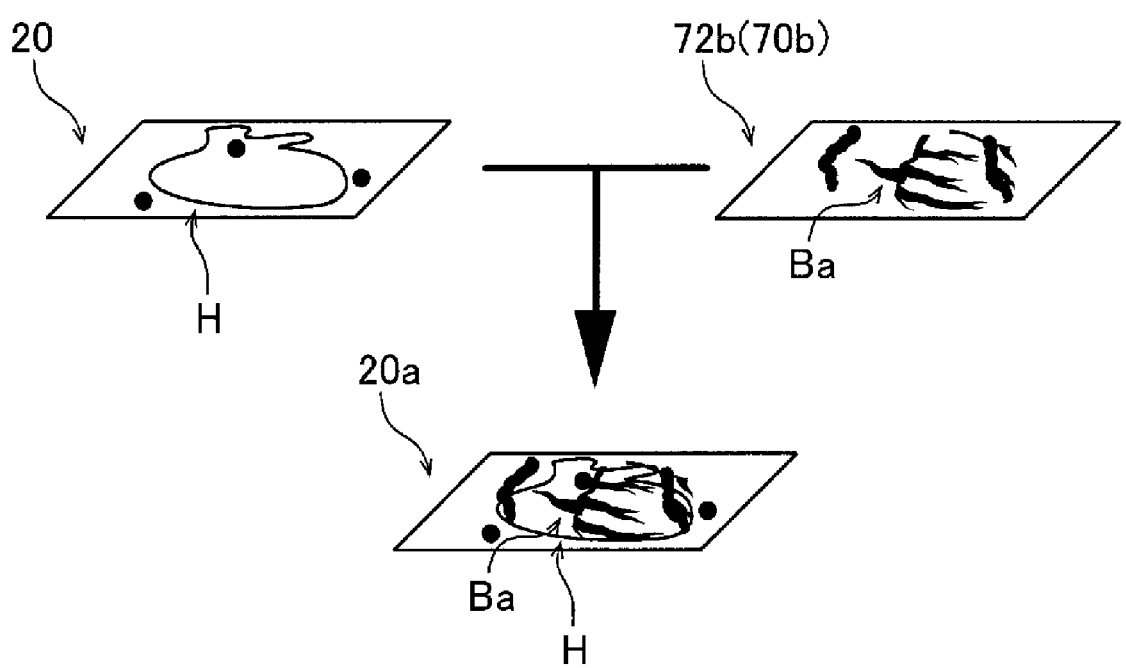
FIG. 10 is a diagram for explaining a superimposed display of a projection image including an image of a contrast agent corresponding to a phase-aligned projection image and a fluoroscopic image.

The phase association unit 15 is configured to associate the fluoroscopic image 20 with one of the series of projection images 70 with respect to the phase in the region (region-of-interest) which periodically moves due to a heartbeat. For this phase association, as shown in FIG. 8 to FIG. 10, three feature points a, b, and c, which are reflected in the fluoroscopic image 20 and the series of post-removal projection images 70a are used. Note that the feature points a, b, and c are granular shadows derived from some structure of the subject P. For example, the phase association unit 15 identifies the periodically moving feature points a (a1, a2, a3, . . . ), b (b1, b2, b3, . . . ), c (c1, c2, c3, . . . ) due to a heartbeat in the post-removal projection image 70a (71a, 72a, 73a, . . . ) generated on the basis of sequentially generated stereoscopic images 50 (51, 52, 53, . . . ). Similarly, the phase association unit 15 identifies the feature points a, b, and c in the fluoroscopic image 20. The phase association unit 15 calculates the post-removal projection image 70a having the feature points most similar to the feature points a, b, and c in the fluoroscopic image 20 from the series of post-removal projection images 70a. Thereafter, the phase association unit 15 associates the projection image 70 corresponding to the calculated post-removal projection image 70a with the fluoroscopic image 20.

Further, the phase association unit 15 is configured to take into account the migration of the region-of-interest in the fluoroscopic image 20 or the post-removal projection image 70a due to breathing that occurs concurrently with the periodic movement of the region (region-of-interest) due to a heartbeat. Thus, the phase association unit 15 may be configured to use not only the similarity of the positions of the specified feature points a, b, and c but also the relative positions of the center of gravity G (G1, G2, G3, . . . ) of the feature points, a, b, and c and the respective feature points, a, b, and c. Thus, it is possible to associate the fluoroscopic image 20 with the post-removal projection image 70a without being affected by the movement of the region-of-interest caused by respiration.

Specifically, as shown in FIG. 8, the phase association unit 15 identifies the featured points a (a1, a2, a3, . . . ), b (b1, b2, b3, . . . ), and c (c1, c2, c3, . . . ) in the series of post-removal projection images 70a (71a, 72a, 73a, . . . ) using a batch image.

Specifically, using a patch image (of a square having an arbitrary size centered on feature points) around the respective feature points a, b, and c, the phase association unit 15 performs matching on whether the patch image around the feature points a, b, and c in the fluoroscopic image 20 and the patch image around the feature points a, b, and c in the post-removal projection image 70 correspond with each other. This matching is performed by, for example, using a method, such as, e.g., normalized cross-correlation. Then, it is identified whether the feature points a, b, and c in the matched fluoroscopic image 20 correspond to which of the feature points a, b, and c in the post-removal projection image 70a.

The phase association unit 15 calculates the center of gravity G (G1, G2, G3, . . . ) of the feature points a, b, and c in each of identified post-removal projection images 70a. Then, as shown in FIG. 9, the phase association unit 15 calculates a vector group showing the positions of the feature points a, b, and c based on the center of gravity G in the series of post-removal projection images 70a.

Here, a vector group showing the positions of the feature points a, b, and c on the basis of the center of gravity G in the fluoroscopic image 20 is also calculated based on the feature points a, b, and c and the center of gravity G of the feature points a, b, and c in the fluoroscopic image 20. Then, the post-removal projection image 70a having a vector group most similar to the vector group calculated from the feature points a, b, and c in the fluoroscopic image 20 is calculated from the series of post-removal projection images 70a (71a, 72a, 73a, . . . ). Then, the projection image 70 corresponding to the calculated post-removal projection image 70a is associated with the fluoroscopic image 20 as a phase-associated projection image. In FIG. 9, the vector group calculated from the feature points a, b, and c in the fluoroscopic image 20 is most similar to the vector group calculated from the feature points a2, b2, and c2 in the post-removal projection image 72a. FIG. 9 shows an example in which the fluoroscopic image 20 is associated with the projection image 72 corresponding to the post-removal projection image 72a.

In the X-ray fluoroscopic imaging apparatus 100 of this embodiment, as described above, when associating the fluoroscopic image 20 with any one of the series of projection images 70, it is configured to use a series of post-removal projection images 70a not containing the image Ba of the contrast agent. For example, the control unit 5 is configured to associate the fluoroscopic image 20 with the projection image 70 in which at least a part of the post-removal projection image 70a in which the image Ba of the contrast agent has been removed and at least a part of the fluoroscopic image 20 are most similar. Thus, the image Ba of the contrast agent is not used for the phase association. Therefore, this suppresses the feature points, b, and c which are used for the phase association from becoming difficult to be identified due to the reflection of the image Ba of the contrast agent.

Further, in the X-ray fluoroscopic imaging apparatus 100 of this embodiment, the series of projection images 70 (71, 72, 73, . . . ) are configured such that a periodically moving region-of-interest is more than one cycle. That is, the CT image data acquisition unit 11 is configured to acquire (collect) the stereoscopic image 50 for generating the projection image 70 so that the periodic movement of the region-of-interest is greater than one cycle.

The image superimposing unit 16 is configured such that the projection image 70 associated with the fluoroscopic image 20 can be superimposed on the fluoroscopic image 20. For example, as shown in FIG. 10, the image superimposing unit 16 can superimpose the superimposing projection image 70b (projection image 70) on the fluoroscopic image 20. In FIG. 10, the superimposing projection image 72b corresponding to the projection image 72 associated with the fluoroscopic image 20 is superimposed on the fluoroscopic image 20 to generate a superimposed image 20a.

The control unit 5 is configured to control the image generation unit 3 to display the superimposed image 20a generated in the image superimposing unit 16 on the display unit 4. With this, in the X-ray fluoroscopic imaging apparatus 100 of this embodiment, the projection image 70 (superimposing projection image 70b) in which at least a part of the generated projection image 70 is most similar to at least a part of the fluoroscopic image 20 can be superimposed on the fluoroscopic image 20. Accordingly, it is possible to suppress the positional displacement between the actual blood vessel and the image Ba of the contrast agent to be superimposed.

The control unit 5 associates one of the series of projection images 70 with the series of fluoroscopic images 20 (21, 22, 23, . . . ) with respect to the phase of a region-of-interest that moves periodically. The control unit 5 sequentially superimposes the projection image 70 (superimposing projection image 70b) on the fluoroscopic image 20 to generate the superimposed image 20a for phase association. The control unit 5 sequentially controls the image generation unit 3 for generating the superimposed image 20a to display the superimposed image 20a on the display unit 4. Accordingly, in the X-ray fluoroscopic imaging apparatus 100 of this embodiment, even in the moving image 30 obtained by connecting the fluoroscopic images 20, the image Ba of the contrast agent can be superimposed on the fluoroscopic image 20 with the displacement from the actual blood sell position suppressed.

(Flow of Phase Association of Fluoroscopic Image and Projection Image and Superimpose Display)

Figure 11:
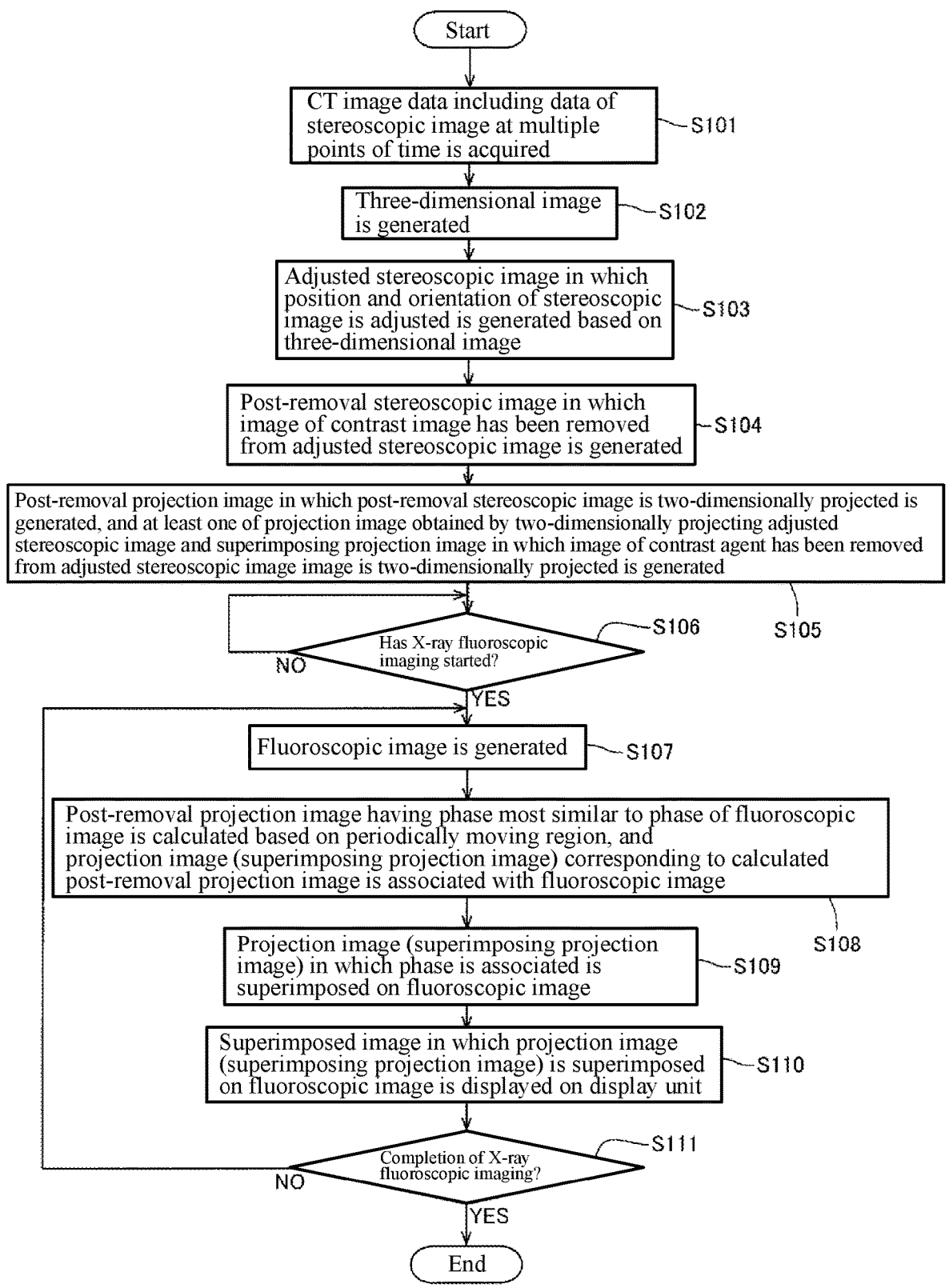
FIG. 11 is a diagram for explaining a control flow by a control unit for displaying a projection image and a fluoroscopic image in a superimposed manner by performing the phase alignment thereof.

Next, with reference to FIG. 11, a control flow by the control unit 5 will be described in which the projection image 70 and the fluoroscopic image 20 are phase-aligned and displayed in a superimposed manner.

First, in Step S101, the control unit 5 (CT image data acquisition unit 11) acquires CT imaging data including stereoscopic images 50 at multiple points of time from outside the X-ray fluoroscopic imaging apparatus 100.

Next, in Step S102, the control unit 5 generates a three-dimensional image 40 by performing X-ray fluoroscopic imaging while rotationally moving the imaging unit 2 in the Y-Z plane by controlling the imagining unit drive mechanism.

Next, in Step S103, the control unit 5 (stereoscopic image adjustment unit 12) generates a series of adjusted stereoscopic image 50a. These series of adjusted stereoscopic images 50 are images in which the orientation and position of the series of stereoscopic images 50 have been adjusted based on the three-dimensional image 40 so that the orientation and position of the subject P reflected in the stereoscopic image 50 and the orientation and position of the subject P reflected in the three-dimensional image 40 match.

Next, in Step S104, the control unit 5 (specific region removal unit 13) generates a series of post-removal stereoscopic image 50b in which the image B of the contrast agent has been removed from the series of adjusted stereoscopic images 50a.

Next, in Step S105, the control unit 5 (projection image generation unit 14) generates a post-removal projection image 70a in which a series of post-removal stereoscopic images 50b have been two-dimensionally projected (the image B of the contrast agent has been removed). Further, the control unit 5 (projection image generation unit 14) generates at least one of the projection image 70 (in which the image B of the contrast agent has not been removed) obtained by two-dimensionally projecting the adjusted stereoscopic image 50a and the superimposing projection image 70b (in which a portion other than the image Ba of the contrast agent has been removed) obtained by two-dimensionally projecting the image B of the contrast agent when generating the post-removal stereoscopic image 50b.

Subsequently, in Step S106, the control unit 5 determines whether the X-ray fluoroscopic imaging has started based on an instruction from a user or an operation of the imaging unit 2. Although the processing up to Step S105 may be performed in real-time, it is preferable that the processing up to Step S105 has been completed prior to Step S106 in order to reduce the control load of Step S105.

In Step S106, when it is determined that the X-ray fluoroscopy has started, in Step S107, the control unit 5 controls the image generation unit 3 to generate the fluoroscopic image 20.

Next, in Step S108, the control unit 5 (phase association unit 15) calculates the post-removal projection image 70a having a phase most similar to the phase of the fluoroscopic image 20 from the series of post-removal projection images 70a based on periodically moving regions. Then, the control unit 5 (phase association unit 15) associates the projection image 70 (superimposing projection image 70b) corresponding to the calculated post-removal projection image 70a with the fluoroscopic image 20.

Next, in Step S109, the control unit 5 generates a superimposed image 20a in which the phase-associated projection image 70 (superimposing projection image 70b) is superimposed on the fluoroscopic image 20.

Next, in Step S110, the control unit 5 controls the image generation unit 3 to display the superimposed image 20a in which the projection image 70 (superimposing projection image 70b) is superimposed on the display unit 4.

Subsequently, in Step S111, the control unit 5 determines whether the X-ray fluoroscopy has been completed based on the instruction from the user or the operation of the imaging unit 2. In Step S111, when it is not determined that the X-ray fluoroscopy has been completed, the process returns to Step S107 to repeat the processing. In Step S111, when it is determined that the X-ray fluoroscopy has been completed, the processing of the phase association between the fluoroscopic image 20 and the projection image 70 and the superimposed display are terminated.

Effects of this Embodiment

In this embodiment, the following effects can be obtained.

In this embodiment, as described above, the control unit 5 associates the projection image 70 in which at least a part of the post-removal projection image 70a in which the image Ba of the contrast agent has been removed and at least a part of the fluoroscopic image 20 are most similar. With this, the superimposing projection image 70b (projection image 70) in which at least a part of the generated projection image 70 is most similar to at least a part of the fluoroscopic image 20 can be superimposed on the fluoroscopic image 20. As a result, even in cases where the region-of-interest includes a blood vessel that moves periodically, it is possible to suppress the positional displacement between the actual blood vessel and the image Ba of the contrast agent to be superimposed. Accordingly, even in the moving image 30 obtained by connecting the fluoroscopic images 20, the image Ba of the contrast agent can be superimposed on the moving image 30 in a state in which the positional displacement between the actual blood vessel and the image Ba of the contrast agent is suppressed. In addition, when associating the fluoroscopic image 20 with the projection image 70, by using the post-removal projection image 70a in which the image Ba of the contrast agent has been removed, the image Ba of the contrast agent which is not used to associate the fluoroscopic image 20 with the projection image 70 can be excluded. With this, it is possible to easily identify the feature points a, b, and c used for the above-described association other than the image Ba of the contrast agent reflected in the projection image 70. As a result, the association between the fluoroscopic image 20 and the projection image 70 can be easily performed.

Further, in this embodiment, as described above, the projection image generation unit 14 generates the two-dimensional projection image 70 from each of the stereoscopic images 50 of the subject obtained from the outside at multiple points of time. With this, the stereoscopic image 50 of the subject P can be collected using a device suitable for sequentially capturing the stereoscopic image 50 of the subject P and different from the X-ray fluoroscopic imaging apparatus 100 to acquire the stereoscopic image 50 at multiple points of time. As a result, it is not required to provide the configuration for sequentially capturing stereoscopic images 50 of the subject P different from the configuration for performing X-ray fluoroscopic imaging in the X-ray fluoroscopic imaging apparatus 100.

Further, in this embodiment, as described above, the projection image generation unit 14 generates the two-dimensional projection image 70 from the stereoscopic image 50 so that the orientation of the subject P in the stereoscopic image 50 is substantially the same as the orientation of the subject P from which the fluoroscopic image 20 is generated. With this, even in cases where the orientation of the subject P in the collected stereoscopic image 50 does not match the current orientation of the subject P from which the fluoroscopic image 20 is generated, the projection image 70 obtained by projecting the stereoscopic image 50 in which the orientation of the subject P is adjusted to match the current orientation of the subject P can be associated with the fluoroscopic image 20. As a result, the fluoroscopic image 20 and the projection image 70 can be more accurately associated with each other.

Further, in this embodiment, as described above, the region-of-interest includes a region that periodically moves due to a heartbeat of a heart H or a respiratory beat. Note that the heartbeat of the heart H or the respiratory beat causes a periodic movement of the blood vessel. For this reason, in cases where the region-of-interest includes a region which periodically moves due to a heartbeat of the heart H or the respiratory beat, there is likely to cause a positional displacement between the actual blood vessel and the image Ba of the contrast agent to be displaced in a superimposed manner. Accordingly, it is particularly effective to apply the present invention, in which the fluoroscopic image 20 including a region-of-interest is generated and the projection image 70 in which at least a part of the projection image 70 is most similar to at least a part of the fluoroscopic image 20 is superimposed on the fluoroscopic image 20 and display the superimposed image, to the X-ray fluoroscopic imaging apparatus 100 which images the subject so that the region that periodically moves due to the heartbeat of the heart H or the respiratory beat is included, as described above.

Also in this embodiment, as described above, the stereoscopic image 50 is collected to include at least one cycle of a periodic motion of a periodically moving region. With this, it is possible to prevent occurrence of the case in which there exists no projection image 70 similar to the fluoroscopic image 20 with respect to the periodically moving region in the region-of-interest. As a result, it is possible to assuredly superimpose the projection image 70 in which the region which periodically moves is most similar on the fluoroscopic image 20 and display the superimposed image.

Further, in this embodiment, as described above, the stereoscopic image 50 is acquired by CT imaging. This allows easy acquisition of stereoscopic images 50 of the subject P at multiple points of time by CT imaging suitable for sequential capturing the stereoscopic images 50 of the subject P.

[Modifications]

It should be understood that the embodiment disclosed here is an example in all respects and are not restrictive. The scope of the present invention is shown by the claims rather than the descriptions of the embodiment described above, and includes all changes (modifications) within the meaning of the scope of claims and equivalent thereof.

In the above-described embodiment, it is configured such that the stereoscopic image 50 is acquired (collected) from the outside (CT imaging apparatus) of the X-ray fluoroscopic imaging apparatus 100, but the present invention is not limited thereto. In the present invention, it may be configured such that the X-ray fluoroscopic imaging apparatus 100 itself is provided with a function of performing CT imaging of the inside of the subject P.

In the above-described embodiment, it is configured such that the stereoscopic image 50 is acquired (collected) from the CT imaging apparatus, but the present invention is not limited thereto. In the present invention, it is not limited to use a CT imaging apparatus, and for example, an MRI (nuclear magnetic resonance imaging) or a PET (positron emission tomography) may also be used as long as it is possible to acquire (collect) a stereoscopic image 50.

Further, in the above-described embodiment, it is configured such that the post-removal projection image 70a and the fluoroscopic image 20 are associated by using the post-removal projection image 70a in which the image Ba of the contrast agent has been removed, but the present invention is not limited thereto. In the present invention, it may be configured such that the projection image 70 in which the image Ba of the contrast agent has not been removed is directly associated with the fluoroscopic image 20h. In this case, it is not necessary to generate the post-removal projection image 70a in which the image Ba of the contrast agent has been removed. Therefore, the processing for superimposing the projection image 70 on the fluoroscopic image 20 can be simplified.

Further, in the above-described embodiment, an example is shown in which the stereoscopic image adjustment unit 12 generates an adjusted stereoscopic image 50a in which the orientation and position of the heart H of the subject P in the stereoscopic image 50 are adjusted based on the region with less periodic movements around the heart H. However, the present invention is not limited thereto. In the present invention, the stereoscopic image adjustment unit 12 may be configured to generate the adjusted stereoscopic image 50a by adjusting only the orientation of the heart H of the subject P in the stereoscopic image 50. In this case, when the phase association unit 15 associates the fluoroscopic image 20 with the projection image 70, the relative positions of the center of gravity G of the feature points a, b, and c and the respective feature points a, b, and c may be used. With this, it is enough to solve the positional displacement between the subject P in the projection image 70 and the subject P in the fluoroscopic image 20 due to the positional displacement between the subject P in the stereoscopic image 50 and the subject P in the fluoroscopic image 20.

Further, in the above-described embodiment, it is configured such that three feature points, a, b, and c are used to associate the fluoroscopic image 20 with the projection image 70, but the present invention is not limited thereto. In the present invention, the number of feature points may be two, four, or more.

Further, in the above-described embodiment, it is configured such that the three-dimensional image 40 is generated by performing X-ray fluoroscopic imaging of the subject P while rotatably moving the imaging unit 2 in the Y-Z plane, but the present invention is not limited thereto. In the present invention, in order to generate the three-dimensional image 40, the imaging unit 2 may be configured to perform X-ray fluoroscopic imaging of the subject P while rotatably moving the imaging unit 2 in the X-Z plane, or the X-ray fluoroscopic imaging of the subject P may be performed while rotatably moving the top board 1 in the Y-Z plane or the X-Z plane.

Further, in the above-described embodiment, it is configured such that after generating the adjusted stereoscopic image 50a in which the orientation and position of the stereoscopic image 50 are adjusted, the post-removal stereoscopic image 50b in which the image B of the contrast agent has been removed from the adjusted stereoscopic image 50a, and the post-removal projection image 70a (in which the image Ba of the contrast agent is not reflected) is generated from the post-removal stereoscopic image 50b. However, the present invention is not limited thereto. In the present invention, it may be configured such that the projection image 70 in which the image Ba of the contrast agent is reflected is generated from the adjusted stereoscopic image 50a and the post-removal projection image 70a in which the image Ba of the contrast agent has been removed is generated from the projection image 70.

Further, in the above-described embodiment, for the sake of convenience of explanation, a flow-driven type flow in which the processing of the control unit 5 is performed in sequence along the process flow is described, but the present invention is not limited thereto. In the present invention, the processing of the control unit 5 may be performed by an event-driven type (event-driven type) processing that performs processing on an event-by-event basis. In this case, the processing of the control unit 5 may be performed in a complete event-driven fashion or in combination of event-driven type processing and flow-driven type processing.

DESCRIPTION OF SYMBOLS

2a: X-ray tube device (irradiation unit)
2b: X-ray receiver (detection unit)
3: image generation unit
4: display unit
5: control unit
13: projection image generation unit
16: image superimposing unit (superimposed image generation unit)
20 (21, 22, 23): fluoroscopic image
20a: superimposed image
50 (51, 52, 53): stereoscopic image
70 (72): projection image
70a (71a, 72a, 73a): post-removal projection image
100: X-ray fluoroscopic imaging apparatus (radiographic imaging apparatus)
B, Ba: image of a contrast agent
H: heart
P: subject

The invention claimed is:

1. A radiographic imaging apparatus comprising:
an irradiator configured to irradiate at least a region-of-interest in a subject with radiation;
a detector configured to detect the radiation which has transmitted through the subject;
a display configured to display a fluoroscopic image including the region-of-interest based on an output of the detector;
a projection image generation unit configured to generate two-dimensional projection images, the two-dimensional projection images each derived from three-dimensional images collected at multiple points of time with a contrast agent being administered to at least a part of the region-of-interest;
a controller configured to associate one two-dimensional projection image of the generated two-dimensional projection images with the fluoroscopic image; and
a superimposed image generator configured to generate a superimposed image by superimposing the fluoroscopic image and the one two-dimensional projection image associated with the fluoroscopic image,
wherein the display is further configured to display the superimposed image,
wherein the projection image generation unit is configured to generate post-removal two-dimensional projection images from the three dimensional images in which an image of the contrast agent has been each removed, and
wherein when the controller is configured to associate the one two-dimensional projection image of the generated two-dimensional projection images with the fluoroscopic image, the controller is configured to:
compare each of the post-removal two-dimensional projection images with the fluoroscopic image to identify one of the post-removal two-dimensional projection images, which has the highest degree of similarity between the post-removal two-dimensional projection image and the fluoroscopic image,
retrieve one two-dimensional projection image corresponding to the identified post-removal two-dimensional projection image among the two-dimensional projection images, and
associate the one two-dimensional projection image retrieved from among the two-dimensional projection images with the fluoroscopic image.

2. The radiographic imaging apparatus as recited in claim 1,
wherein the projection image generation unit generates the two-dimensional projection images from the three-dimensional images of the subject collected from outside of the radiographic imaging apparatus at the multiple points of time.

3. The radiographic imaging apparatus as recited in claim 1,
wherein the projection image generation unit generates the two-dimensional projection images from the three-dimensional images so that at least an orientation of the subject in the three-dimensional images matches an orientation of the subject in the fluoroscopic image.

4. The radiographic imaging apparatus as recited in claim 1,
wherein the region-of-interest includes a region that periodically moves due to a heartbeat or a respiratory beat.

5. The radiographic imaging apparatus as recited in claim 4,
wherein the three-dimensional images include at least one cycle of a periodic motion of the periodically moving region .

6. The radiographic imaging apparatus as recited in claim 1,
wherein the three-dimensional images collected at the multiple points of time are acquired by CT imaging.

7. A method of radiographic imaging, comprising:
irradiating a subject, including a region-of-interest in the subject, with radiation;
detecting radiation that has been transmitted through the subject;
based on the detected radiation, generating a fluoroscopic image including the region-of-interest;
providing a plurality of three-dimensional images, obtained at different points in time from one another, the plurality of three-dimensional images being of the subject in a state in which a contrast agent was administered to the subject;
for each of the plurality of three-dimensional images, generating a set of two-dimensional projection images, each set of two-dimensional projection images including a first two-dimensional projection image and a corresponding second two-dimensional projection image in which an image of the contrast agent has been removed;
selecting one first two-dimensional projection image among the first two-dimensional projection images;
generating a superimposed image by superimposing the fluoroscopic image and the selected one first two-dimensional projection image; and
displaying the superimposed image,
wherein the selecting the one first two-dimensional projection image among the first two-dimensional projection images comprises:
comparing each of the second two-dimensional projection images with the fluoroscopic image to identify one of the second two-dimensional projection images, which has the highest degree of similarity between the second two-dimensional projection image and the fluoroscopic image,
retrieving one first two-dimensional projection image corresponding to the identified second two-dimensional projection image among the first two-dimensional projection images, and
associating the retrieved first two-dimensional projection image with the fluoroscopic image, and
selecting the associated first two-dimensional projection image as the one first two-dimensional projection image.

8. The method of claim 7,
wherein the steps of irradiating a subject, detecting radiation that has been transmitted through the subject, and generating the fluoroscopic image are performed by a first radiographic imaging apparatus, and
wherein the plurality of three-dimensional images are provided to the first radiographic imaging apparatus from a source external to the first radiographic imaging apparatus.

9. The method of claim 7, wherein generating the set of two-dimensional projection images for each of the three-dimensional images comprises, for each three-dimensional image, determining a relationship of an orientation of the subject in the three-dimensional image and an orientation of the subject in the fluoroscopic image.

10. The method of claim 7, wherein the region-of-interest includes a region that includes a periodic motion resulting from at least one of a heartbeat or a respiratory beat of the subject.

11. The method of radiographic imaging according to claim 7, comprising:
irradiating a subject, including a region-of-interest in the subject, the region-of-interest including a region that periodically moves due to at least one of a heartbeat and a respiratory beat of the subject;
generating a series of fluoroscopic images including the region-of-interest; and
for each generated fluoroscopic image, generating the superimposed image and displaying the superimposed image to thereby display a moving image including the series of fluoroscopic images superimposed with corresponding first two-dimensional projection images.

12. The method of claim 10, wherein the plurality of three-dimensional images respectively represent internal structure of the subject at corresponding different points in time within one cycle of the periodic motion.

13. The method of claim 7, wherein the plurality of three-dimensional images are obtained from a CT imaging apparatus.

14. The method of claim 7, further comprising performing CT imaging with a CT imaging apparatus to obtain the plurality of three-dimensional images.

15. The method of claim 14,
wherein the steps of irradiating a subject, detecting radiation that has been transmitted through the subject, and generating the fluoroscopic image are performed by a first radiographic imaging apparatus that is separate from the CT imaging apparatus.

\* \* \* \* \*